US012019053B2

(12) United States Patent
Adams et al.

(10) Patent No.: US 12,019,053 B2
(45) Date of Patent: Jun. 25, 2024

(54) SYSTEMS AND METHODS FOR ANALYZING MULTIPHASE PRODUCTION FLUID

(71) Applicant: Saudi Arabian Oil Company, Dhahran (SA)

(72) Inventors: Robert Adams, Houston, TX (US); Thomas Hillman, Houston, TX (US)

(73) Assignee: Saudi Arabian Oil Company, Dhahran (SA)

(*) Notice: Subject to any disclaimer, the term of this patent is extended or adjusted under 35 U.S.C. 154(b) by 135 days.

(21) Appl. No.: 17/841,058

(22) Filed: Jun. 15, 2022

(65) Prior Publication Data
US 2023/0408388 A1    Dec. 21, 2023

(51) Int. Cl.
*G01N 3/12* (2006.01)
*G01N 3/06* (2006.01)
*G01N 33/28* (2006.01)

(52) U.S. Cl.
CPC .......... *G01N 3/12* (2013.01); *G01N 3/06* (2013.01); *G01N 33/2823* (2013.01); *G01N 2203/0611* (2013.01)

(58) Field of Classification Search
CPC ........ G01N 3/12; G01N 3/06; G01N 33/2823; G01N 2203/0611
See application file for complete search history.

(56) References Cited

U.S. PATENT DOCUMENTS

| 4,852,395 A | * | 8/1989 | Kolpak | .............. G01N 33/2823 73/861.04 |
| 5,086,643 A | * | 2/1992 | Marek | ................ G01N 15/0826 73/38 |

(Continued)

FOREIGN PATENT DOCUMENTS

| CN | 203847106 U | 9/2014 |
| CN | 102405398 B | 8/2016 |

(Continued)

OTHER PUBLICATIONS

Ramsey, H.J., Jr., "Rapid Methods for Estimating Reservoir Compressibilities," JPT 447, Trans., AIME, 231, Apr. 1964.

*Primary Examiner* — Kristina M Deherrera
*Assistant Examiner* — Jean F Morello
(74) *Attorney, Agent, or Firm* — DINSMORE & SHOHL LLP

(57) ABSTRACT

Systems and methods for analyzing a multiphase production fluid includes a pipeline, a fluidic measurement chamber, a pressure sensor, a temperature sensor, an actuating unit, and a fluidic control unit. The actuating unit is partially disposed in the fluidic measurement chamber and is movable between an expansion stage in the fluidic measurement chamber and a compression stage in the fluidic measurement chamber. The fluidic control unit is in communication with the fluidic measurement chamber, the pressure sensor, the temperature sensor, and the actuating unit. The fluidic control unit is configured to communicate with the pipeline to supply the multiphase production fluid to the fluidic measurement chamber. The fluidic control unit is further configured to communicate with the pressure sensor to detect a first pressure of the multiphase production fluid in the fluidic measurement chamber at the expansion stage.

20 Claims, 4 Drawing Sheets

(56) References Cited

U.S. PATENT DOCUMENTS

| | | | |
|---|---|---|---|
| 5,442,948 A | 8/1995 | Cowing | |
| 5,932,792 A | 8/1999 | Dougherty | |
| 6,874,351 B2 | 4/2005 | Bloder et al. | |
| 7,257,985 B2 | 8/2007 | Franda et al. | |
| 7,591,191 B2 | 9/2009 | Hewitt et al. | |
| 7,866,201 B1 | 1/2011 | Tutu | |
| 8,109,127 B2 | 2/2012 | Gysling et al. | |
| 2015/0040658 A1* | 2/2015 | Abyzov | G01F 25/00 |
| | | | 73/199 |
| 2018/0217101 A1* | 8/2018 | Hopper | G01N 29/326 |
| 2020/0319005 A1 | 10/2020 | Folgero et al. | |

FOREIGN PATENT DOCUMENTS

| | | |
|---|---|---|
| CN | 2012931578 U | 4/2021 |
| WO | 2009093927 A1 | 7/2009 |

\* cited by examiner

SYSTEMS AND METHODS FOR ANALYZING MULTIPHASE PRODUCTION FLUID

TECHNICAL FIELD

The present disclosure relates to the analysis of multiphase production fluids and, more particularly, to the analysis of multiphase flow in the oil and gas industries, where multiphase flow often involves the simultaneous flow of oil, water and gas.

BACKGROUND

Multiphase flow occurs in almost all producing oil and gas wells and surface pipes that transport produced fluids. The present disclosure introduces a novel way to obtain gas volume fractions and gas/liquid flow rates in a multiphase production fluid. The system does not require calibration and can give results that are very close to ground truth measurements. Generally, the systems and methodology of the present disclosure contemplate the use of a fluidic measurement chamber that can be coupled to a surface production pipe carrying the multiphase production fluid.

SUMMARY

Systems that monitor multiphase flow rates and phase fractions may be limited during operation with their accuracy, with their operating envelope, or both. In particular, systems that prioritize measuring the gas phase of the multiphase flow may suffer as the ratio of the liquid phase in the multiphase flow increases. Accordingly, systems that prioritize measuring the liquid phase of the multiphase flow may suffer as the ratio of the gas phase in the multiphase flow increases. There is a need for a system which accurately measures a gas phase of the multiphase flow by measuring varying characteristics of the gas phase throughout a complete range of gas volume fractions and liquid phase fractions in a cost-effective manner. The system may determine an oil volume fraction and a water volume fraction by measuring varying characteristics of the oil and water volume fractions, respectively, to determine a volume fraction of each phase of the multiphase fluid and a flow rate of the multiphase fluid.

According to the subject matter of the present disclosure, a system for analyzing a multiphase production fluid is provided where a gas phase of the multiphase production fluid is determined by measuring varying parameters of the gas phase of the multiphase production fluid at a first position within an actuating unit and at a second position of the actuating unit. A composite sensor may also determine an oil phase of the multiphase production fluid and a water phase of the multiphase production fluid to determine the phase fractions of the multiphase production fluid.

In accordance with one embodiment of the present disclosure is directed to a system for analyzing a multiphase production fluid, the system including a pipeline, a fluidic measurement chamber, a pressure sensor, a temperature sensor, an actuating unit, and a fluidic control unit. The pipeline is configured to supply the multiphase production fluid to the fluidic measurement chamber. The actuating unit is partially disposed in the fluidic measurement chamber and is movable between an expansion stage in the fluidic measurement chamber and a compression stage in the fluidic measurement chamber. The fluidic control unit is in communication with the fluidic measurement chamber, the pressure sensor, the temperature sensor, and the actuating unit. The fluidic control unit is configured to communicate with the pipeline to supply the multiphase production fluid to the fluidic measurement chamber. The fluidic control unit is further configured to communicate with the pressure sensor to detect a first pressure of the multiphase production fluid in the fluidic measurement chamber at the expansion stage. The fluidic control unit is further configured to communicate with the temperature sensor to detect a first temperature of the multiphase production fluid in the fluidic measurement chamber at the expansion stage. The fluidic control unit is further configured to communicate with the actuating unit to translate from the expansion stage to the compression stage. The fluidic control unit is further configured to communicate with the pressure sensor to detect a second pressure of the multiphase production fluid in the fluidic measurement chamber at the compression stage. The fluidic control unit is further configured to communicate with the temperature sensor to detect a second temperature of the multiphase production fluid in the fluidic measurement chamber at the compression stage. The fluidic control unit is further configured to convert the first pressure, the first temperature, the second pressure, and the second pressure of the multiphase production fluid into a gas volume of the multiphase production fluid.

In accordance with another embodiment of the present disclosure, methods for analyzing a multiphase production fluid performed by a fluidic control unit. The method includes supplying multiphase production fluid from a pipeline to a fluidic measurement chamber in an expansion stage. The method further includes detecting a first pressure of the multiphase production fluid in the fluidic measurement chamber during the expansion stage via a pressure sensor. The method further includes detecting a first temperature of the multiphase production fluid in the fluidic measurement chamber during the expansion stage via a temperature sensor. The method further includes translating an actuating unit from the expansion stage to a compression stage. The method further includes detecting a second pressure of the multiphase production fluid in the fluidic measurement chamber during the compression stage via the pressure sensor. The method further includes detecting a second temperature of the multiphase production fluid in the fluidic measurement chamber during the compression stage via the temperature sensor. The method further includes converting the first temperature, the first pressure, the second temperature and the second pressure of the multiphase production fluid into a gas volume of the multiphase production fluid in the fluidic measurement chamber.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
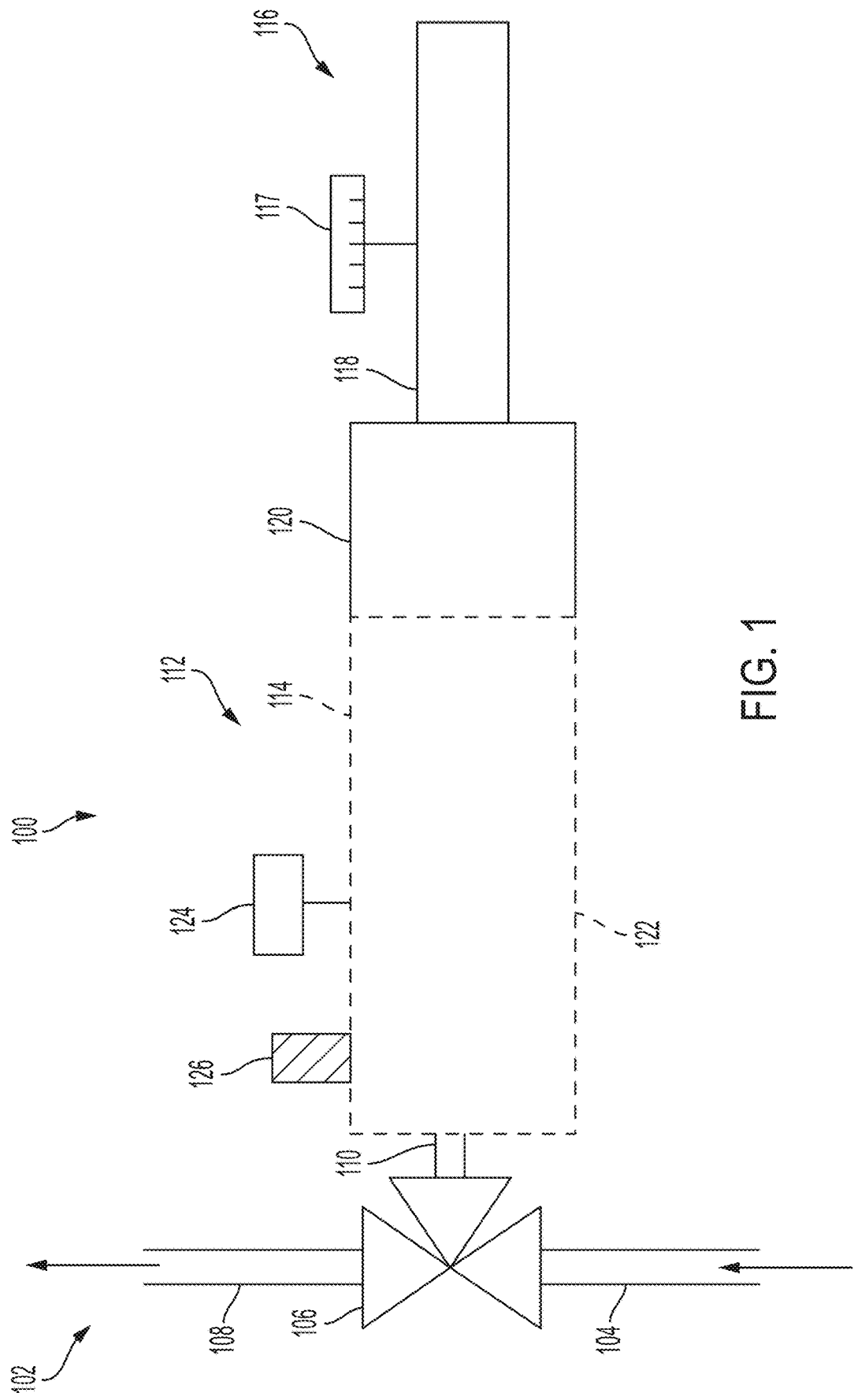
FIG. 1 illustrates systems and methodology for analyzing a multiphase production fluid at a first measurement position, according to some embodiments of the present disclosure.
Figure 2:
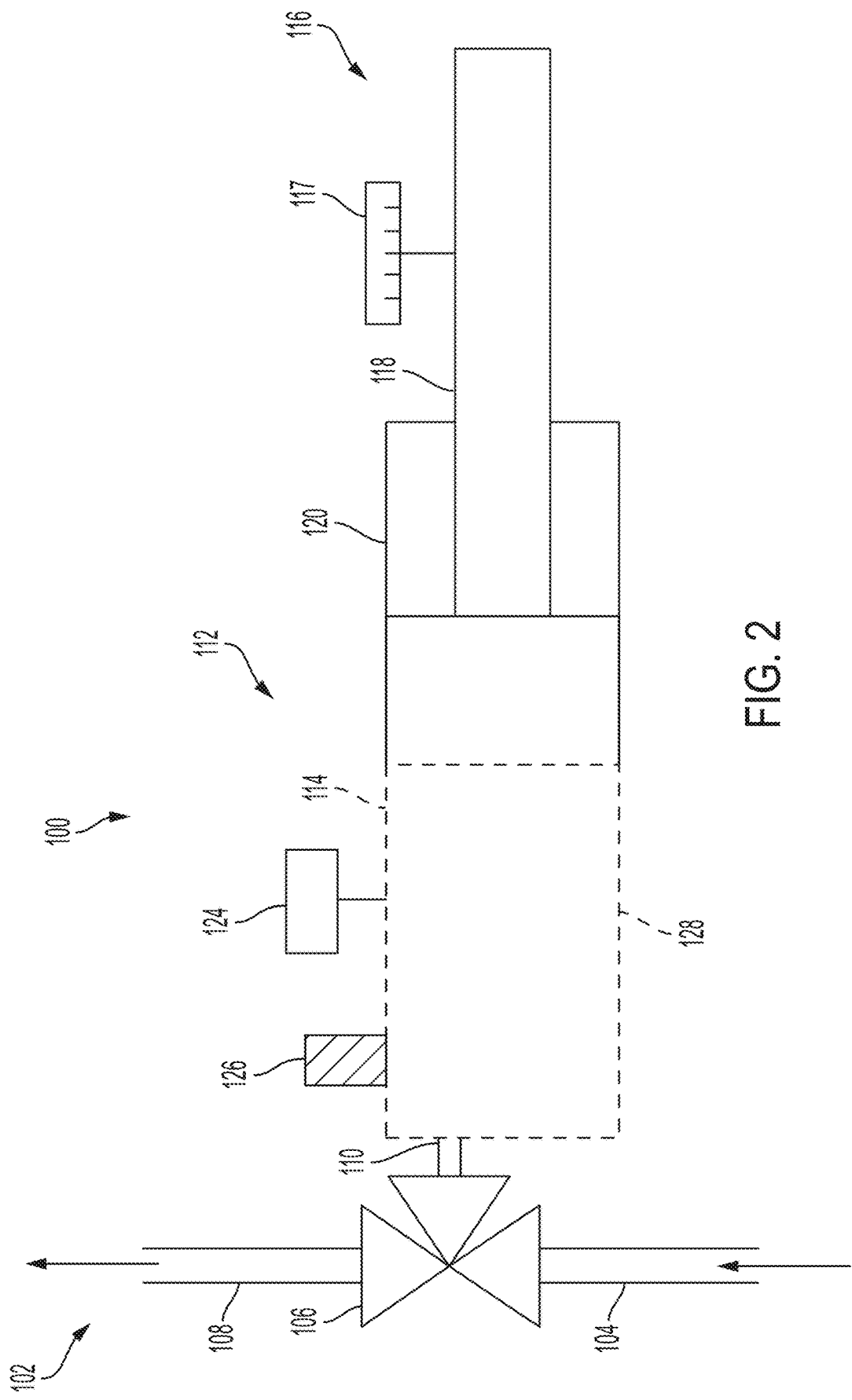
FIG. 2 illustrates systems and methodology for analyzing a multiphase production fluid at a second measurement position, according to some embodiments of the present disclosure.

Referring initially to FIGS. 1 and 2, a system 100 and method having a fluidic control unit for analyzing a multiphase production is shown according to some embodiments of the present disclosure. The system 100 may include a pipeline 102, a fluidic measurement chamber 112, an actuating unit 116, a pressure sensor 124, and a composite sensor 126.

The pipeline 102 includes an inlet 104, a valve 106, an outlet 108, and a chamber inlet 110. Multiphase production fluid from a surface production conduit enters into the pipeline 102 from the inlet 104. During production, the multiphase production fluid interfaces with the valve 106, which directs the multiphase production fluid to the outlet 108.

When the multiphase production fluid is to be tested for its volume fractions of oil, gas, and water, the fluidic control unit provides a signal to the valve 106 to divert multiphase production fluid to the chamber inlet 110. The chamber inlet 110 is fluidly coupled to the fluidic measurement chamber 112 and is configured to provide the multiphase production fluid to the fluidic measurement chamber 112.

The fluidic measurement chamber 112 includes a fluid chamber 114 for receiving the multiphase production fluid for the fluidic measurement chamber 112 via the chamber inlet 110. The fluid chamber 114 defines a first volume 122 at a first measurement position. The fluidic control unit provides multiphase production fluid to the fluidic measurement chamber 112 until the fluid chamber 114 is filled, such that the volume of the multiphase production fluid is equal to the first volume 122 at the first measurement position.

The fluidic control unit may then provide a signal to the pressure sensor 124 to detect pressure of the multiphase production fluid in the fluidic measurement chamber during the first measurement position.

The fluidic control unit may then provide a signal to the composite sensor 126 to detect an oil volume and a water volume of the multiphase production fluid in the fluidic measurement chamber during the first measurement position.

In embodiments, during an isothermal process (e.g., a process involving or possessing a constant temperature), the composite sensor 126 includes a liquid phase sensor configured to detect the oil volume and the water volume of the multiphase production fluid in the fluidic measurement chamber.

The liquid phase sensor may be any number of sensing types which are sensitive to the liquids content of a multiphase production fluid. In embodiments, the liquid phase sensor differentiates oil/water content in liquids through electromagnetic permittivity sensing methods. In embodiments, the liquid phase sensor uses differentiates oil/water content in liquids through density sensing methods.

In embodiments, the composite sensor 126 includes a sound speed sensor configured to detect the oil volume and the water volume of the multiphase production fluid in the fluidic measurement chamber. The sound speed sensor includes an acoustic transducer pair to measure the travel time of an acoustic pulse through the multiphase production fluid over a length of the fluid chamber 114. By analyzing a difference in travel time of the acoustic pulse, the sound speed sensor is able to differentiate oil/water content in the fluid chamber 114. In these embodiments, the pressure sensor 124 may not be required for detecting the gas volume of the multiphase production fluid.

As discussed in greater detail herein, in embodiments, the composite sensor 126 may include a weight sensor which is used to determine the oil volume and the water volume.

The actuating unit 116 is partially disposed in the fluidic measurement chamber 112 and is movable between the first measurement position in the fluidic measurement chamber 112 and a second measurement position in the fluidic measurement chamber 114. During the second measurement position, the actuating unit 116 may translate towards the multiphase production fluid to compress the multiphase production fluid or may translate away from the multiphase production fluid to expand the multiphase production. After determining the first volume 122, a first pressure from the pressure sensor 124, and the oil volume and the water volume of the multiphase production fluid from the composite sensor 126, the fluidic control unit provides a signal to the actuating unit 116 to translate to the second measurement position. After moving to the second measurement position, the fluid chamber 114 defines a second volume 128.

The actuating unit 116 may include a piston body 118, a piston head 120, and a position sensor 117. The piston head 120 is configured to apply a force upon the fluid chamber 114 to adjust the width of the fluid chamber 114, thereby expanding or contracting the volume of the fluid chamber 114. The piston head 120 is movable along a piston body 118. The position sensor 117 measures a position of the piston head 120 along the piston body 118. In this way, the position sensor 117 may be used to determine a volume of the fluid chamber 114. In these embodiments, the position sensor 117 provides a signal indicative of the position of the piston head 120 to the fluidic control unit. In embodiments, the actuating unit 116 is a telescoping pipe (not shown) that adjusts the volume of the fluid chamber 114 by adjusting a diameter of the fluid chamber 114 from the first measurement position to the second measurement position.

After the actuating unit 116 moves to the second measurement position, the multiphase production fluid may define a different pressure and a different liquid/oil phase ratio. The fluidic control unit provides a signal to the pressure sensor 124 to provide a second pressure of the multiphase production fluid during the second measurement position. The fluidic control unit also provides a signal to the composite sensor 126 to provide detect the oil volume and the water volume of the multiphase production fluid during the second measurement position.

During an isothermal process, the gas volume during the first measurement position $V_{g1}$ of the multiphase production fluid may be determined using Equation 1:

$$V_{g1} = -\frac{1}{C_T}\left(\frac{V_2 - V_1}{P_2 - P_1}\right) \qquad \text{Equation 1}$$

Using equation 1, the second volume 128 and the first volume 122 are equal to $V_2$ and $V_1$, respectively. Additionally, the second pressure measured in the second measurement position is equal to $P_2$ and the first pressure measured in the first measurement position is equal to $P_1$. In an isothermal process, the isothermal compressibility $C_T$ of a fluid phase is a known constant that is derived from the molecular weight of a hydrocarbon gas mixture. Accordingly, a $C_T$ of the gas volume may be used as a constant value.

When the composite sensor 126 is the sound velocity sensor, the gas volume during the first measurement position $V_{g1}$ of the multiphase production fluid may be determined using Equation 2:

$$V_{g1} = \left(\frac{\beta_G V_2}{\beta_L - \beta_G}\right) \cdot \left(\frac{c_2 V_1}{c_1 V_2}\right)^2 - \left(\frac{\beta_G V_1}{\beta_L - \beta_G}\right) \qquad \text{Equation 2}$$

Using equation 2, the second volume 128 and the first volume 122 are equal to $V_2$ and $V_1$, respectively. Additionally, an adiabatic bulk module of the gas $\beta_G$ and the adiabatic bulk module of the oil and water $\beta_L$ are known constants. The sound speed sensor determines a first sound speed $c_1$ of the multiphase production fluid during the first measurement position a second sound speed $c_2$ of the multiphase production fluid during the second measurement position.

When the composite sensor 126 is the sound velocity sensor, the actuating unit 116 provides a compressive force onto the fluid chamber 114, such that the gas volume is compressed until it is substantially equal to zero during the second measurement position. In this way, the volume of the oil and the volume of the water phases may be determined using the sound velocity sensor using equations 3 and 4, the sound speed of oil $c_O$ and the sound speed of water $c_W$ are known constants.

$$V_O = V_1 \left(\frac{c_2 - c_W}{c_O - c_W}\right) \qquad \text{Equation 3}$$

$$V_W = V_1 - V_O \qquad \text{Equation 4}$$

As the gas volume is determined using Equation 1 and the oil volume and the water volume are determined through the composite sensor, the ratio of each phase of the multiphase production fluid may then be determined. The gas volume, the oil volume, and the water volume may then be used to determine production fluid phase volume fraction data, production fluid phase flow rate data, or both by also considering a cross-sectional area of the pipeline.

Figure 3:
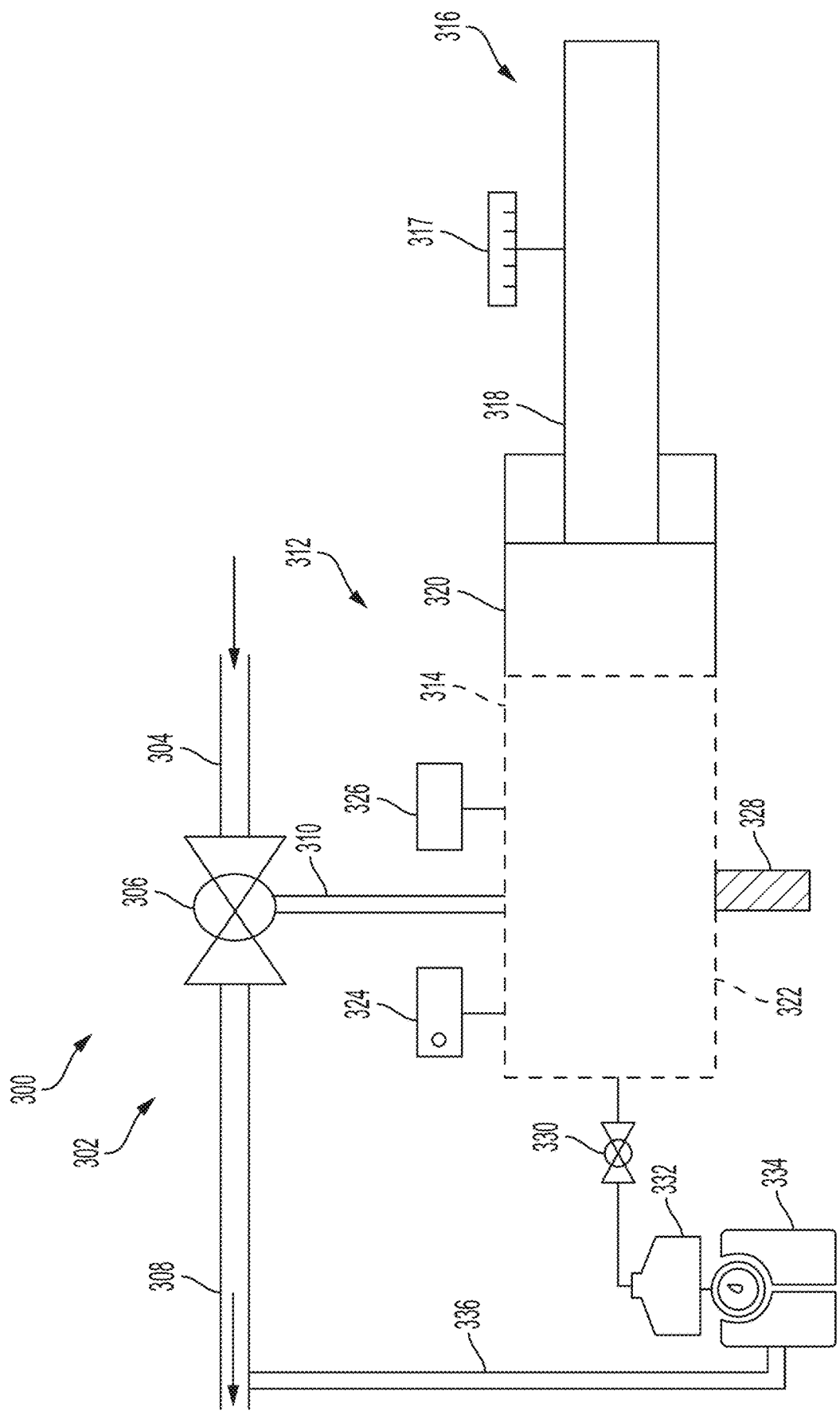
FIG. 3 illustrates systems and methodology for analyzing a multiphase production fluid during an expansion stage, according to some embodiments of the present disclosure.
Figure 4:
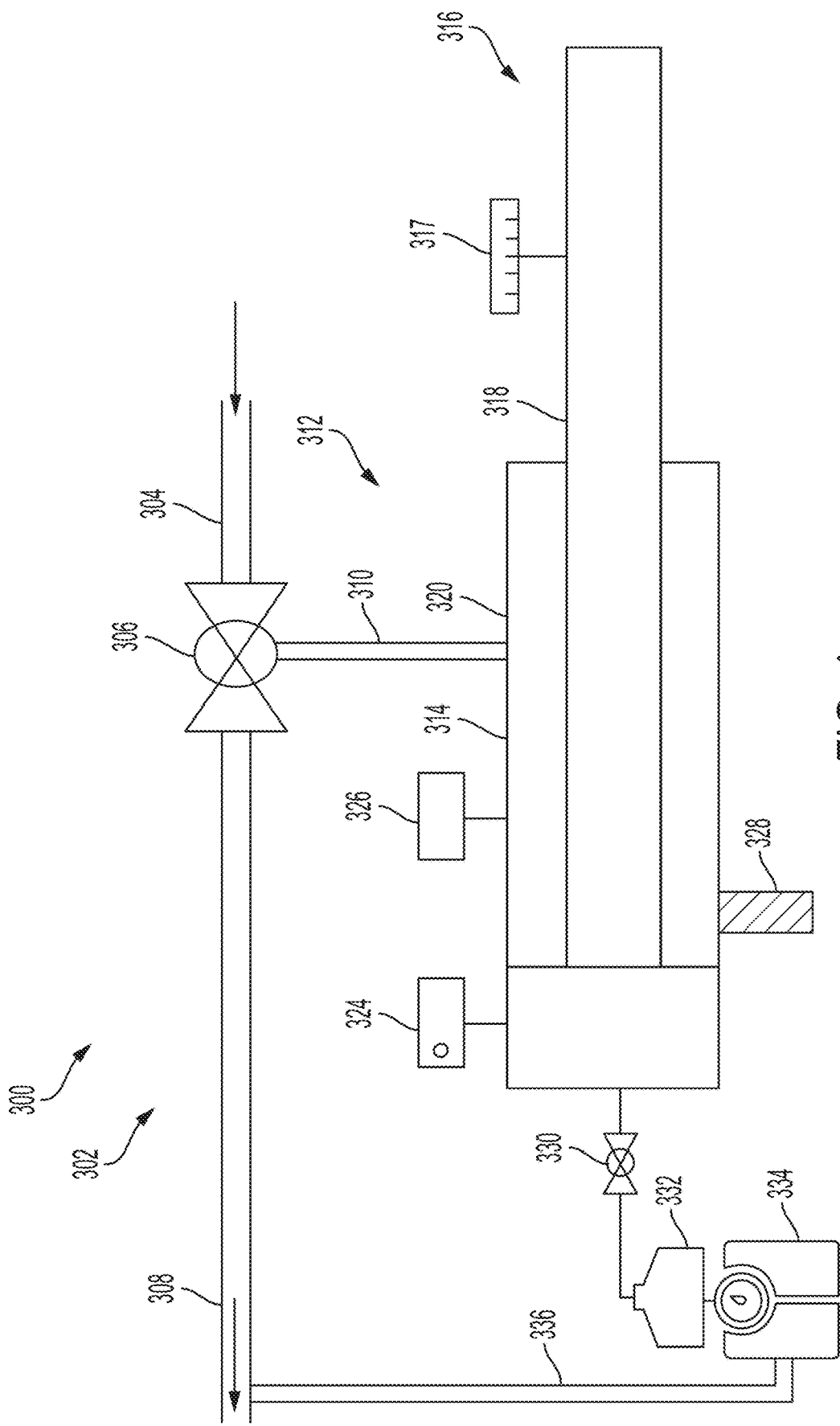
FIG. 4 illustrates systems and methodology for analyzing a multiphase production fluid during a compression stage, according to some embodiments of the present disclosure.

Referring now to FIGS. 3 and 4, a system 300 and method having a fluidic control unit for analyzing a multiphase production, is shown according to some embodiments of the present disclosure. The system 300 may include a pipeline 302, a fluidic measurement chamber 312, an actuating unit 316, a pressure sensor 324, a temperature sensor 326, a density sensor 328, a tank valve 330, a tank 332, a weight sensor 334, and a return pipeline 336.

The pipeline 302 includes an inlet 304, a valve 306, an outlet 308, and a chamber inlet 310. Multiphase production fluid from a surface production conduit enters into the pipeline 302 from the inlet 304. During production, the multiphase production fluid interfaces with the valve 306, which directs the multiphase production fluid to the outlet 308.

When the multiphase production fluid is to be tested for its volume fractions of oil, gas, and water, the fluidic control unit provides a signal to the valve 306 to divert multiphase production fluid to the chamber inlet 310. The chamber inlet 310 is fluidly coupled to the fluidic measurement chamber 312 and is configured to provide the multiphase production fluid to the fluidic measurement chamber 312.

The fluidic measurement chamber 312 includes a fluid chamber 314 for receiving the multiphase production fluid for the fluidic measurement chamber 312 via the chamber inlet 310. The fluid chamber 314 defines a volume 322 during an expansion stage, i.e., when the fluid chamber 314 is in an expanded state. The fluidic control unit provides multiphase production fluid to the fluidic measurement chamber 312 until the fluid chamber 314 is filled, such that the volume of the multiphase production fluid is equal to the volume 322 during the expansion stage, i.e. when in the expanded state.

The fluidic control unit may then provide a signal to the pressure sensor 324 to detect a first pressure of the multiphase production fluid in the fluidic measurement chamber during the expansion stage.

The fluidic control unit may then provide a signal to the temperature sensor 326 to detect a first temperature of the multiphase production fluid in the fluidic measurement chamber during the expansion stage.

The fluidic control unit may then provide a signal to the density sensor 328 to detect a density of the multiphase production fluid in the fluidic measurement chamber during the expansion stage.

The actuating unit 316 is partially disposed in the fluidic measurement chamber 312 and is movable between the expanded state in the fluidic measurement chamber 312, a compressed state in the fluidic measurement chamber 312, and an ejection state in the fluidic measurement chamber 312. During the transition between the expanded state and the compressed state, i.e. in a compression stage, the actuating unit 316 translates towards the multiphase production fluid, thereby compressing the multiphase production fluid in the fluid chamber 314.

The actuating unit 316 may include a piston body 318, a piston head 320, and a position sensor 317. The piston head 320 is configured to apply a force upon the fluid chamber 314 to adjust the width of the fluid chamber 314, thereby expanding or contracting the volume of the fluid chamber 314. The piston head 320 is movable along a piston body 318. The position sensor 317 measures a position of the piston head 320 along the piston body 318. In this way, the position sensor 317 may be used to determine the volume of the fluid chamber 314. In these embodiments, the position sensor 317 provides a signal indicative of the position of the piston head 320 to the fluidic control unit. In embodiments, the actuating unit 316 is a telescoping pipe (not shown) that adjusts the volume of the fluid chamber 314 by adjusting a diameter of the fluid chamber 314.

After determining the volume 322 from the position sensor 317, the first pressure from the pressure sensor 324, a first temperature from the temperature sensor 326, and density from the density sensor 328 of the multiphase production fluid during the expansion stage, the fluidic control unit provides a signal to the actuating unit 316 to translate to the compression stage, thereby compressing the multiphase production fluid in the fluid chamber 314.

The volume 322 of the fluid chamber 314 during the compression stage is determined via the position sensor 317. The fluidic control unit may also determine a second pressure via the pressure sensor 324, and a second temperature via the temperature sensor 326. The fluidic control unit may then provide a signal to the actuating unit 316 to translate to the ejection stage, i.e to translate to the ejection state, thereby ejecting the multiphase production fluid from the fluid chamber 314 to the tank 332.

The fluid chamber 314 is in selective fluid communication with the tank 332 via the tank valve 330. In the expansion stage and the compression stage, the fluidic control unit provides a signal to the tank valve 330 preventing multiphase production fluid from exiting the fluid chamber 314. During the ejection stage, the fluidic control unit provides a signal to the tank valve 330 allowing multiphase production fluid to exit the fluid chamber 314.

The tank 332 is coupled to the weight sensor 334, facilitating for the multiphase production fluid to be measured after entering the tank 332. The fluidic control unit may then receive a signal from the weight sensor 334 of the detected weight of the multiphase production fluid in the fluidic measurement chamber during the ejection stage.

The gas volume during the expansion stage $V_{g1}$ of the multiphase production fluid may be determined using Equation 5:

$$V_{g1} = -\frac{P_2 V_{gc}}{T_2\left(\frac{P_1}{T_1} - \frac{P_2}{T_2}\right)} \qquad \text{Equation 5}$$

The volume $V_{gc}$ is determined by calculating a difference between the volume 322 between the expansion stage and the compression stage. Additionally, the second pressure measured in the expansion stage is equal to $P_2$ and the first pressure measured in the compression stage is equal to $P_1$.

The oil volume $V_O$ of the multiphase production fluid may be determined using Equation 6:

$$V_O = \frac{W - (V_1 - V_{g1})\rho_W}{\rho_O - \rho_W} \qquad \text{Equation 6}$$

Using equation 6, the weight of the multiphase production fluid W is determined via the weight sensor 334. The volume 322 is equal to the volume $V_1$ during the expansion stage and the volume of the gas $V_{g1}$ during the expansion stage is determined using Equation 5. The density of water $\rho_W$ is a known constant. The density of oil $\rho_O$ may be determined by first determining a composition of the oil and then correlating the composition of the oil to known oil densities for the particular oil composition. The oil composition may be independently tested or determined by the location of the oil rig, the depth of the oil reservoirs, or both.

The volume of water may then be determined by calculating a difference between the volume $V_1$ during the expansion stage, the volume of the gas $V_{g1}$ during the expansion stage, and the oil volume $V_O$.

As the gas volume is determined using Equation 5 and the oil volume and the water volume are determined through Equation 6, the ratio of each phase of the multiphase production fluid may then be determined. The gas volume, the oil volume, and the water volume may then be used to determine production fluid phase volume fraction data, production fluid phase flow rate data, or both by also considering a cross-sectional area of the pipeline.

Once measurements of the multiphase production fluid are completed, the multiphase production fluid may exit the tank 332 via the return pipeline 336, where the return pipeline 336 is in fluid communication with the pipeline 302.

It is noted that recitations herein of a component of the present disclosure being "configured" or "programmed" in a particular way, to embody a particular property, or to function in a particular manner, are open-ended, structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for analyzing a multiphase production fluid, the system comprising:
   a pipeline;
   a fluidic measurement chamber;
   a pressure sensor;
   a temperature sensor;
   an actuating unit; and
   a fluidic control unit, wherein,
   the pipeline is configured to supply the multiphase production fluid to the fluidic measurement chamber,
   the actuating unit is partially disposed in the fluidic measurement chamber and is movable between an expanded state of the fluidic measurement chamber and a compressed state of the fluidic measurement chamber, and
   the fluidic control unit is in communication with the fluidic measurement chamber, the pressure sensor, the temperature sensor, and the actuating unit, and is configured to
   communicate with the pipeline to supply the multiphase production fluid to the fluidic measurement chamber,
   communicate with the pressure sensor to detect a first pressure of the multiphase production fluid in the fluidic measurement chamber at the expanded state,
   communicate with the temperature sensor to detect a first temperature of the multiphase production fluid in the fluidic measurement chamber at the expanded state,
   communicate with the actuating unit to translate from the expanded state to the compressed state,
   communicate with the pressure sensor to detect a second pressure of the multiphase production fluid in the fluidic measurement chamber at the compressed state, communicate with the temperature sensor to detect a second temperature of the multiphase production fluid in the fluidic measurement chamber at the compressed state, and convert the first pressure, the first temperature, the second pressure, and the second pressure of the multiphase production fluid into a gas volume of the multiphase production fluid.

2. The system of claim 1, further comprising:
a tank in fluid communication with the fluidic measurement chamber, and
a weight sensor configured to determine a weight of multiphase production fluid disposed in the tank,
wherein the actuating unit is configured to provide the multiphase production fluid in the fluidic measurement chamber to the tank in an ejection state.

3. The system of claim 2, further comprising a valve disposed between the fluidic measurement chamber and the tank, the valve configured to be in selective fluid communication with the fluidic measurement chamber and the tank, wherein:
in the expanded state and in the compressed state, the valve blocks fluid communication between the fluidic measurement chamber and the tank; and
in the ejection state, the valve allows for fluid communication between the fluidic measurement chamber and the tank.

4. The system of claim 1, wherein the actuating unit comprises a piston configured to change a width of the fluidic measurement chamber when translating from the expanded state to the compressed state.

5. The system of claim 1, wherein the actuating unit comprises a telescoping pipe configured to change a diameter of the fluidic measurement chamber when translating from the expanded state to the compressed state.

6. The system of claim 1, wherein the actuating unit comprises a position sensor configured to measure a position of a component of the actuating unit to determine a volume of the multiphase production fluid in the fluidic measurement chamber in the expanded state and in the compressed state.

7. The system of claim 1, wherein the fluidic control unit is configured to convert an oil volume, a water volume, and the gas volume of the multiphase production fluid to production fluid phase volume fraction data, production fluid phase flow rate data, or both by utilising a cross-sectional area of the pipeline.

8. The system of claim 1, further comprising:
a tank in fluid communication with the fluidic measurement chamber, and
a weight sensor configured to determine a weight of multiphase production fluid disposed in the tank,
a valve disposed between the fluidic measurement chamber and the tank, the valve configured to be in selective fluid communication with the fluidic measurement chamber and the tank, wherein:
in the expanded state and in the compressed state, the valve is configured to block fluid communication between the fluidic measurement chamber and the tank,
in an ejection state, the valve is configured to allow for fluid communication between the fluidic measurement chamber and the tank,
the actuating unit is configured to provide the multiphase production fluid in the fluidic measurement chamber to the tank during the ejection state, and
the actuating unit comprises a piston configured to change a width of the fluidic measurement chamber when translating from the expanded state to the compressed state.

9. The system of claim 1, wherein the actuating unit comprises:
a piston head configured to change a width of the fluidic measurement chamber when translating from the expanded state to the compressed state; and
a position sensor configured to measure a position of the piston head to determine a volume of the multiphase production fluid in the fluidic measurement chamber in the expanded state and in the compressed state.

10. The system of claim 1, wherein the actuating unit comprises:
a telescoping pipe configured to change a diameter of the fluidic measurement chamber when translating from the expanded state to the compressed state; and
a position sensor configured to measure a position of a component of the actuating unit to determine a volume of the multiphase production fluid in the fluidic measurement chamber in the expanded state and in the compressed state.

11. The system of claim 1, further comprising:
a tank in fluid communication with the fluidic measurement chamber;
a weight sensor configured to determine a weight of multiphase production fluid disposed in the tank; and
a valve disposed between the fluidic measurement chamber and the tank, the valve configured to be in selective fluid communication with the fluidic measurement chamber and the tank, wherein:
in the expanded state and in the compressed state, the valve is configured to block fluid communication between the fluidic measurement chamber and the tank,
in an ejection state, the valve is configured to allow for fluid communication between the fluidic measurement chamber and the tank,
the actuating unit is configured to provide the multiphase production fluid in the fluidic measurement chamber to the tank during the ejection state, and
the actuating unit comprises:
a piston head configured to change a width of the fluidic measurement chamber when translating from the expanded state to the compressed state, and
a position sensor configured to measure a position of the piston head to determine a volume of the multiphase production fluid in the fluidic measurement chamber in the expanded state and in the compressed state.

12. A method for analyzing a multiphase production fluid performed by a fluidic control unit, the method comprising:
supplying multiphase production fluid from a pipeline to a fluidic measurement chamber in an expanded state;
detecting a first pressure of the multiphase production fluid in the fluidic measurement chamber in the expanded state via a pressure sensor;
detecting a first temperature of the multiphase production fluid in the fluidic measurement chamber in the expanded state via a temperature sensor;
translating an actuating unit from the expanded state to a compressed state;
detecting a second pressure of the multiphase production fluid in the fluidic measurement chamber in the compressed state via the pressure sensor;

detecting a second temperature of the multiphase production fluid in the fluidic measurement chamber in the compressed state via the temperature sensor; and converting the first temperature, the first pressure, the second temperature and the second pressure of the multiphase production fluid into a gas volume of the multiphase production fluid in the fluidic measurement chamber.

13. The method of claim 12, further comprises:

providing the multiphase production fluid in the fluidic measurement chamber to a tank in fluid communication with the fluidic measurement chamber during an ejection state; and measuring a weight of the multiphase production fluid in the tank via a weight sensor.

14. The method of claim 13, further comprises selectively fluidly coupling a valve disposed between the fluidic measurement chamber and the tank, wherein:

in the expanded state and the compressed state, the valve blocks fluid communication between the fluidic measurement chamber and the tank, and in the ejection state the valve allows for fluid communication between the fluidic measurement chamber and the tank.

15. The method of claim 12, wherein the actuating unit comprises a piston configured to change a width of the fluidic measurement chamber when translating from the expanded state to the compressed state.

16. The method of claim 12, wherein the actuating unit comprises a telescoping pipe configured to change a diameter of the fluidic measurement chamber when translating from the expanded state to the compressed state.

17. The method of claim 12, wherein the actuating unit comprises a position sensor configured to measure a position of a component of the actuating unit to determine a volume of the multiphase production fluid in the fluidic measurement chamber in the expanded state.

18. The method of claim 12, further comprising:

providing the multiphase production fluid in the fluidic measurement chamber to a tank in fluid communication with the fluidic measurement chamber during an ejection state;

measuring a weight of the multiphase production fluid in the tank via a weight sensor; and selectively fluidly coupling a valve disposed between the fluidic measurement chamber and the tank, wherein:

in the expanded state and the compressed state, the valve blocks fluid communication between the fluidic measurement chamber and the tank, and in the ejection state, the valve allows for fluid communication between the fluidic measurement chamber and the tank.

19. The method of claim 12, wherein the actuating unit comprises:

a piston head configured to change a width of the fluidic measurement chamber when translating from the expanded state to the compressed state; and a position sensor configured to measure a position of the piston head to determine a volume of the multiphase production fluid in the fluidic measurement chamber in the expanded state.

20. The method of claim 12, wherein the actuating unit comprises:

a telescoping pipe configured to change a diameter of the fluidic measurement chamber when translating from the expanded state to the compressed state; and a position sensor configured to measure a position of a component of the actuating unit to determine a volume of the multiphase production fluid in the fluidic measurement chamber in the expanded state.

* * * * *